US006691387B2

(12) United States Patent
Hanafy

(10) Patent No.: US 6,691,387 B2
(45) Date of Patent: Feb. 17, 2004

(54) METHOD OF USING A TWO-DIMENSIONAL TRANSDUCER ARRAY

(75) Inventor: Amin M. Hanafy, Los Altos Hills, CA (US)

(73) Assignee: Acuson Coporation, Mountain View, CA (US)

( * ) Notice: Subject to any disclaimer, the term of this patent is extended or adjusted under 35 U.S.C. 154(b) by 0 days.

(21) Appl. No.: 10/117,839

(22) Filed: Apr. 8, 2002

(65) Prior Publication Data

US 2002/0108220 A1 Aug. 15, 2002

Related U.S. Application Data

(62) Division of application No. 09/484,760, filed on Jan. 18, 2000, now Pat. No. 6,415,485, which is a continuation of application No. 08/886,962, filed on Jul. 2, 1997, now Pat. No. 6,043,589.

(51) Int. Cl.[7] .......................... H04R 17/00; A61B 8/00

(52) U.S. Cl. .......................... 29/25.35; 29/593; 29/594; 600/443; 600/447; 600/459; 128/916; 310/334; 310/367; 324/727

(58) Field of Search ................................ 29/25.35, 594, 29/583; 600/443, 447, 459; 128/916; 310/334–337, 367, 368; 324/727

(56) References Cited

U.S. PATENT DOCUMENTS

| | | | | |
|---|---|---|---|---|
| 3,833,825 A | | 9/1974 | Haan | |
| 3,959,748 A | * | 5/1976 | Subramanian | 29/25.35 X |
| 4,314,393 A | * | 2/1982 | Wakatsuki et al. | 29/25.35 |
| 5,415,175 A | | 5/1995 | Hanafy et al. | |
| 5,438,998 A | | 8/1995 | Hanafy | |

FOREIGN PATENT DOCUMENTS

| | | | | |
|---|---|---|---|---|
| JP | 56-18778 | * | 2/1981 | 600/447 |

OTHER PUBLICATIONS

Pao et al, "Analysis of a Tapered Phased Array Transducer for 3–D Imaging Applications", IEEE Proceedings, Ultrasonics Symposium, 1991, vol. 1, Dec. 1991, pp. 8–11.*

* cited by examiner

*Primary Examiner*—A. Dexter Tugbang

(57) ABSTRACT

A method of manufacturing a two-dimensional ultrasound transducer array is provided in which the transducer array is formed by a plurality of transducer elements sequentially arranged in the azimuth direction and each transducer element has a non-uniform thickness and each transducer is divided into a left and a right half which can be independently excited.

2 Claims, 6 Drawing Sheets

FIG. 7
2D BULLET SLITTED UPPER 2MHZ

METHOD OF USING A TWO-DIMENSIONAL TRANSDUCER ARRAY

RELATED APPLICATIONS

This application is a divisional pursuant to 37 C.F.R. §1.53(b) of application Ser. No. 09/484,760 filed Jan. 18, 2000 now U.S. Pat. No. 6,415,485, which is a continuation of application Ser. No. 08/886,962 filed Jul. 2, 1997, now U.S. Pat. No. 6,043,589, both of which are herein incorporated by reference.

FIELD OF THE INVENTION

This invention relates to a two-dimensional transducer array and the method of manufacture thereof, and, more particularly, to a two-dimensional transducer array that has a simple construction and operation.

BACKGROUND

It is desirable to provide a broadband transducer that is capable of operating at a wide range of frequencies without a loss in sensitivity. As a result of the increased bandwidth provided by a broadband transducer, the resolution along the range axis may improve, resulting in better image quality. One possible application for a broadband transducer is contrast harmonic imaging. In contrast harmonic imaging, the heart and muscle tissue are clearly visible at a fundamental frequency, however, at the second harmonic, the contrast agent itself can be viewed.

Because contrast harmonic imaging requires that the transducer be capable of operating at a broad range of frequencies (i.e. at both the fundamental and second harmonic), existing transducers typically cannot function at such a broad range. For example, a transducer having a center frequency of 5 Megahertz and having a 60% ratio of bandwidth to center frequency has a bandwidth of 3.5 Megahertz to 6.50 Megahertz. If the fundamental harmonic is 3.5 Megahertz, then the second harmonic is 7.0 Megahertz. Thus, a transducer having a center frequency of 5 Megahertz would not be able to adequately operate at both the fundamental and second harmonic.

In addition to having a transducer which is capable of operating at a broad range of frequencies, two-dimensional transducer arrays are also desirable to increase the resolution of the images produced and allow three-dimensional imaging. An example of a two-dimensional transducer array is illustrated in U.S. Pat. No. 3,833,825 to Haan issued Sep. 3, 1974. Two-dimensional arrays allow for increased control of the excitation of ultrasound beams along the elevation axis which is absent from conventional single-dimensional arrays which only allow for control of the excitation of ultrasound beams along the azimuth axis.

However, two-dimensional arrays are difficult to fabricate because they typically require that each element be cut into several segments along the elevation axis. In addition, separate leads for exciting each of the respective segments must be provided. As an example, Haan describes a two-dimensional transducer array that has 64 elements, 8 segments in both the elevation and azimuth directions (i.e., 8×8 array). Of course 64 leads must also be provided to excite each of the 64 segments. This results in an 8-fold increase in the number of leads needed compared to a conventional single-dimensional array. If more segments are provided, more interconnecting leads must also be provided. In addition, such a two-dimensional array requires rather complicated software in order to excite each of the several segments at appropriate times during the ultrasound scan.

Also, because of the numerous diced segments in N×N arrays such as that described in Haan there results a very high impedance which makes it very difficult to electrically match the transducer to the ultrasound system which typically has a low impedance.

Conventional one-dimensional arrays have been used to perform two-dimensional scanning. In order to scan two-dimensionally, the array must include a positioner or provide for mechanical registration of the transducer's location in order to identify the location of each scan. Real-time three-dimensional imaging is therefore not possible with conventional one-dimensional transducers since all of the scan information is processed after it has been acquired. In addition, using a conventional one-dimensional transducer to perform two-dimensional scanning requires that the transducer be physically moved or tilted in position as each frame is acquired. Typically one frame can be acquired in about 33 milliseconds. It takes much longer than that for a human operator to physically move or tilt the transducer from scan to scan. Thus, the possibility of performing real or quasi-real time three-dimensional imaging is comprised. Also, the accuracy and reliability of positioners and mechanical registration can compromise the ability to obtain three-dimensional imaging.

It is therefore desirable to provide a two-dimensional transducer array that has the performance of an N×N array without the complexity of requiring N×N number of hardware channels or cables.

It is also desirable to provide a two-dimensional transducer array that is simple to manufacture and operate.

It is also desirable to provide a two-dimensional transducer array that can generate real-time three-dimensional images.

It is also desirable to provide a two-dimensional transducer that has a low impedance and therefore can be easily and inexpensively electrically matched to an ultrasound system.

SUMMARY

According to a first aspect of the invention there is provided a transducer for producing an ultrasound beam upon excitation. The transducer includes a plurality of transducer elements, each of the transducer elements having a width in an elevation direction extending from a first end to a second end and a thickness of each transducer element is at a minimum at a point about midway between the first end and the second end of the element and the thickness is at a maximum at the first and the second end. An azimuthal kerf extends through each transducer element at the point about midway between the first end and the second end of each transducer element.

According to a second aspect of the invention there is provided a transducer for producing an ultrasound beam upon excitation. The transducer includes an acoustically attenuated backing block having a top surface, a flex circuit disposed on the top surface of the backing block and a plurality of transducer elements disposed on the flex circuit. The plurality of transducer elements are sequentially arranged in an azimuth direction. Each transducer element has a left half and a right half where the left and right half are electrically and acoustically isolated from one another so that each half can be individually and independently excited and wherein the thickness of the transducer element is non-uniform.

According to a third aspect of the invention there is provided a transducer for producing an ultrasound beam upon excitation. The transducer includes a plurality of transducer elements, each of the transducer elements having a width in an elevation direction extending from a first end to a second end and a thickness in a range direction. The thickness of each transducer element is non-uniform. An azimuthal kerf extends through each transducer element and divides the transducer element into a left and a right half.

According to a fourth aspect of the invention there is provided a method of making a transducer for producing an ultrasound beam upon excitation. The method includes the steps of providing a plurality of transducer elements, each of the transducer elements having a width in an elevation direction extending from a first end to a second end and a thickness in a range direction wherein the thickness of each transducer element is at a minimum at a point about midway between the first and second end of the element and the thickness is at a maximum at the first and second end, and dicing an azimuthal key through each transducer element at the point about midway between the first and second end of each transducer element.

According to a fifth aspect of the invention there is provided a method of making a transducer for producing an ultrasound beam upon excitation. The method includes the steps of providing an acoustically attenuated backing block having a top surface, disposing a flex circuit on the top surface of the backing block, disposing a plurality of transducer elements on the flex circuit wherein the transducer elements are sequentially arranged in an azimuth direction wherein the thickness of the transducer element is non-uniform, and dividing each transducer element into a left half and a right half wherein the left and right halves are electrically and acoustically isolated from each other.

According to a sixth aspect of the invention there is provided a method of making a transducer for producing an ultrasound beam upon excitation. The method includes the steps of providing a plurality of transducer elements, each transducer element having a width in an elevation direction extending from a first end to a second end and a thickness in a range direction wherein the thickness of each transducer element is non-uniform, and dicing an azimuthal kerf through each transducer element to divide each transducer element into a left and a right half.

According to a seventh aspect of the invention there is provided a method for two-dimensional scanning to produce three-dimensional images. The method includes the steps of providing a plurality of transducer elements sequentially arranged in an azimuth direction wherein each transducer has a left and a right half that are electrically and acoustically isolated from one another so that the left and the right half can be independently excited, the plurality of transducer elements having a non-uniform thickness in the range direction, applying an excitation signal to only the left half of the plurality of transducer elements, progressively increasing the frequency of the excitation signal applied to the left half of the transducer elements, coupling the left and right half of the transducer elements to a high frequency excitation signal, applying an excitation signal to only the right half of the transducer elements, and progressively decreasing the frequency of the excitation signal applied to the right half of the transducer elements.

DETAILED DESCRIPTION OF THE PRESENTLY PREFERRED EMBODIMENTS

Figure 1:
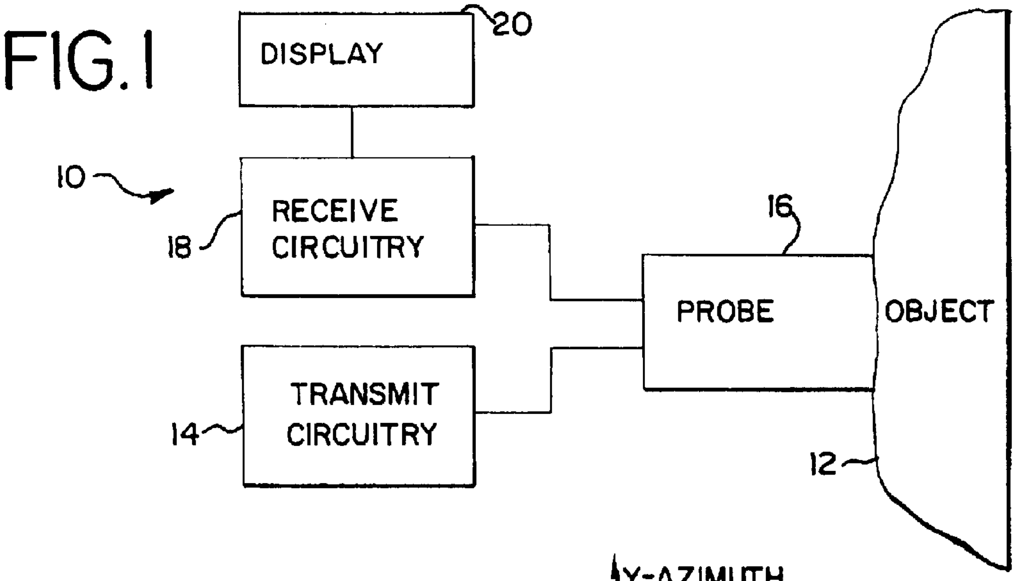
FIG. 1 is a schematic view of an ultrasound system for generating an image of an object or body being observed.

Referring now to the accompanying drawings, in FIG. 1 there is provided a schematic view of an ultrasound system 10 for generating an image of an object or body 12 being observed. The ultrasound system 10 has transmit circuitry 14 for transmitting electrical signals to the transducer probe 16, receive circuitry 18 for processing the signals received by the transducer probe, and a display 20 for providing the image of the object 12 being observed.

Figure 2:
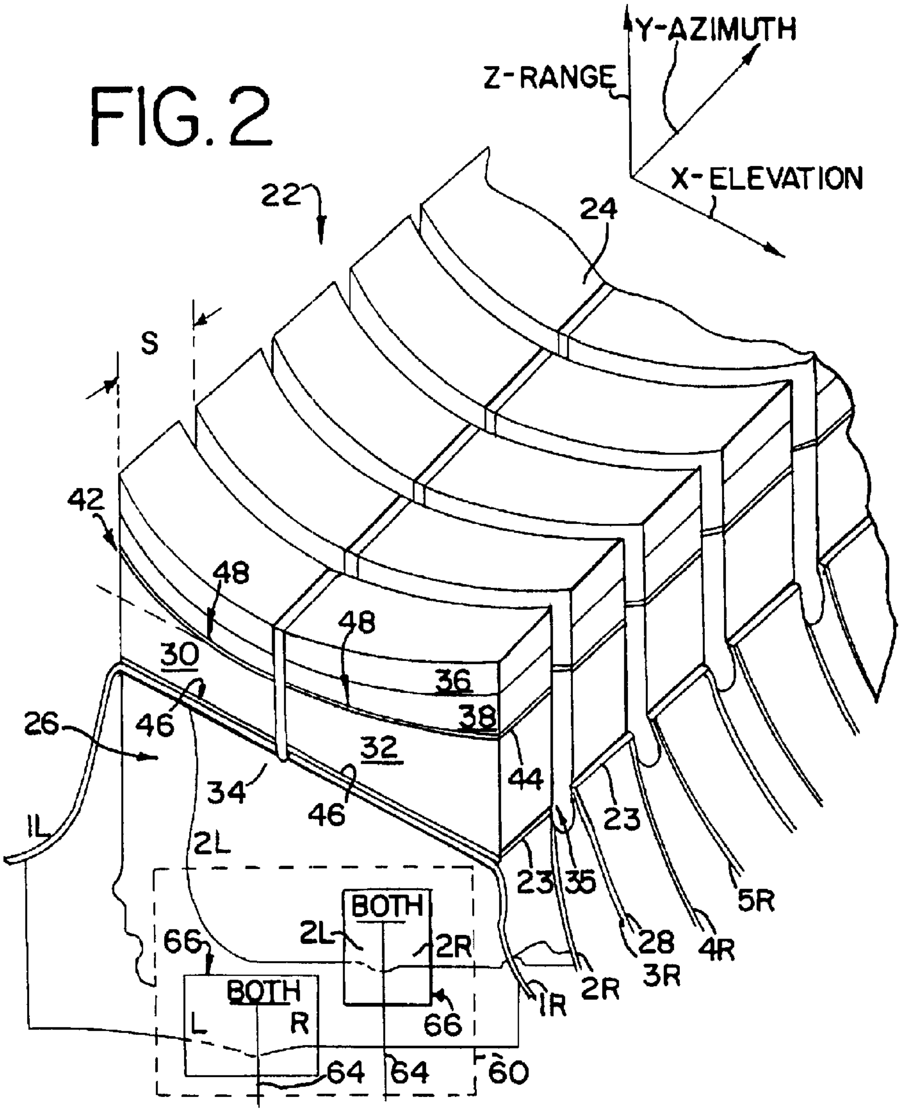
FIG. 2 is a perspective view of a portion of a transducer array according to a preferred embodiment of the present invention.

FIG. 2 is a perspective view of a portion of transducer array located in the probe 16 according to a preferred embodiment of the present invention. The transducer array 22 has a plurality of transducer elements 24 sequentially arranged along the y-azimuth axis. Typically, there are one hundred twenty-eight elements 24, however, the array may have any number of transducer elements. Also provided is a backing block 26 and a flex circuit 28 disposed on a top surface of the backing block 26. The transducer elements 24 are disposed on the flex circuit 28 which will be described in greater detail hereinafter.

In a preferred embodiment two matching layers 36 and 38 are also provided. Matching layer 38 is disposed on the top surface of each transducer element 24 and preferably has a high impedance. Matching layer 36 is disposed on matching layer 38 and preferably has a low impedance. Both matching layers have a width extending in the x-elevation direction from a first end 42 of the transducer element 24 to a second end 44 of the transducer element and a thickness extending in the z-range direction. The thickness of each matching layer is non-uniform and, preferably, is a maximum at the first and second ends, 42 and 44, and is a minimum at a point midway or substantially midway between the first and second ends.

In a preferred embodiment, the shape and dimension of the matching layers 36 and 38 are approximated by the equation LML=(½) (LE)(CML/CE) where, for a given point on the transducer surface, LML is the thickness of the individual matching layer, LE is the thickness of the transducer element, CML is the speed of sound of the matching layer, and CE is the speed of sound of the transducer element.

Each transducer element 24 has an electrode 46 formed on a first surface of the element and another electrode 48 formed on an opposite surface as is well known to those of ordinary skill in the art.

In a preferred embodiment the transducer array is composed of the following elements. The transducer elements 24 are composed of piezoelectric material lead zirconate titanate (PZT), however, the transducer elements 24 may be composed of other materials such as a composite like polyvinylidene fluoride (PVDF), an electro-restrictive material such as lead magnesium niobate (PMN) or a composite ceramic material or other suitable material. The high impedance matching layer 38 is formed of Dow Coming's epoxy resin DER 332 with Dow Coming's hardener DEH 24 filled with 9 micron alumina oxide particles from Microabrasive of Westfield, Mass. and 1 micron tungsten carbide particles available from Cerac Incorporated of Milwaukee, Wis. The low impedance matching layer 36 is formed of Dow Coming's epoxy resin DER 332 with Dow Coming's hardener DEH 24.

Each of the plurality of transducer elements 24 is divided into two electrically and acoustically isolated segments or halves, a left segment 30 and a right segment 32, by a kerf 34 diced through the matching layers 36 and 38, the transducer elements 24 and the flex circuit 28. The kerf 34 extends in the azimuth direction. The azimuth kerf 34 preferably also extends slightly into the backing block 26 to ensure the electrical and acoustic isolation between the left and right segments 30 and 32 of the transducer elements 24 as shown. The transducer elements 24 are electrically and acoustically isolated from each other in the azimuth direction by dicing kerfs 35 as is commonly done in the industry. The kerfs 35 may also slightly extend into the backing block 26 to ensure the electrical and acoustic isolation between transducer elements 24 in the azimuth direction.

Each transducer element 24 has a width extending in the x-elevation direction from the first end 42 to the second end 44 and a thickness extending in the z-range direction. The thickness of each transducer element 24 is non-uniform and, in a preferred embodiment, each element 24 has a maximum thickness at the first and second ends 42 and 44 and a minimum thickness, midway or substantially midway between the first and second ends.

The transducer array shown in FIG. 2 utilizes the technology described in U.S. Pat. Nos. 5,415,175 and 5,438,998, which are hereby specifically incorporated by reference and assigned to the present assignee. The '175 and '998 patents described similar transducer array having transducer elements of non-uniform thickness. It was discovered that by using non-uniform thickness transducer elements, the size of the elevation aperture could be varied by varying the frequency of the signal used to excite the transducer elements. More particularly, for high frequency signals, only the thinner middle section of the transducer element generated an exiting beam thus producing a beam with a narrow elevation aperture. As the frequency of the applied signal is lowered, the thicker portions of the transducer element also became excited thereby generating a beam having a wider aperture. Thus, by controlling the excitation frequency of the applied signal, the operator of the ultrasound system could control which section of transducer element generated the ultrasound beam. At higher excitation frequencies the beam is primarily generated from the center of the transducer element and at lower excitation frequencies the beam is primarily generated from the entire transducer element.

Figure 3:
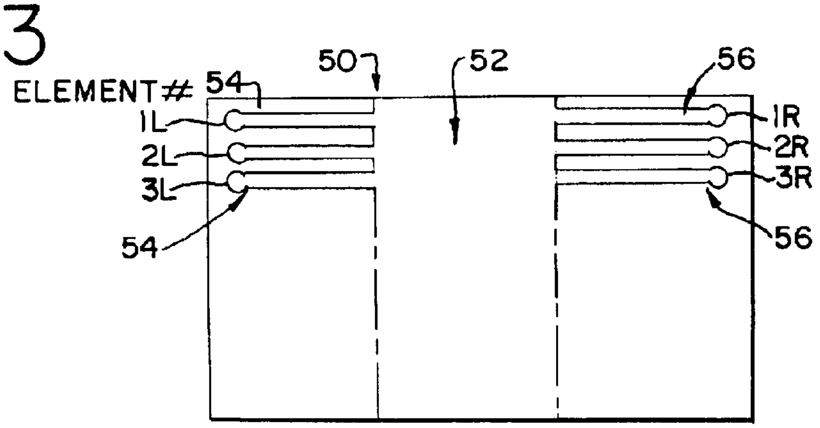
FIG. 3 is a top view of the flex circuit according to a preferred embodiment of the present invention.

FIG. 3 is a top view of a flex circuit according to a preferred embodiment of the present invention. The flex circuit 50 is disposed between the backing block 26 and transducer elements 24 shown in FIG. 2. The flex circuit 50 has a center pad area 52 on which the electrode 46 of the transducer elements will be disposed when all of the components are assembled. Extending from the left and right sides of the center area 52 are a plurality of left traces 54 and right traces 56 respectively. The left traces 54 are aligned with the right traces 56 and there are as many traces as there are segments. As already described in a preferred embodiment 128 transducer elements are sequentially arranged in the azimuth direction and each transducer element is divided in half thereby requiring 256 traces in total.

To construct the transducer array shown in FIG. 2 the flex circuit 50 shown in FIG. 3 is disposed on the top surface of the backing block 26 so that the center pad area 52 is flat on the top surface and the left and right traces 54 and 56 extend over the sides of the backing block 26. Electrodes 46 and 48 would be deposited on two opposite surfaces of a slab of piezoelectric material as is well known to those of ordinary skill in the art. The slab of piezoelectric material is positioned on the flex circuit 50 so that electrode 46 is in contact with the center pad area 52 of the flex circuit 50. A ground circuit (not shown) would then be disposed on electrode 48. The two acoustic matching layers 36 and 38 are then disposed on the ground circuit. Then kerfs 34 and 35 are diced through the acoustic matching layers 36 and 38, ground circuit, transducer elements 24, a flex circuit 50 and into the backing block 26 to electrically and acoustically isolate the transducer elements 24 from each other and electrically and acoustically isolate the two segments 30 and 32 of each transducer element 24.

Returning to FIG. 2, an excitation signal can be applied to the left half of a transducer element, the right half of a transducer element or both halves simultaneously. In order to accomplish this, a switching device 60 is provided. In a preferred embodiment the switching device 60 is a multiplexer although it could also be a programmable gate array or any other solid-state device with three position switching capability. The switching device 60 is incorporated into the head of the transducer (not shown) and is coupled to the left and right traces 54 and 56 of the flex circuit 50 as shown. The switching device 60 is also coupled to a cable 62 which can be coupled to the transmit and receive circuitry shown in FIG. 1. Within the cable 62 is preferably one coaxial wire 64 for each transducer element 24 and two leads for the switching element 60. Thus the number of wires 64 within the cable 62 is only increased by two from a conventional one-dimensional transducer array. Within the switching device 60 is a three-way switch 66 that allows each coaxial wire 64 to be coupled to either the left trace 54, the right trace 56 or both the left and right traces.

Figure 4:
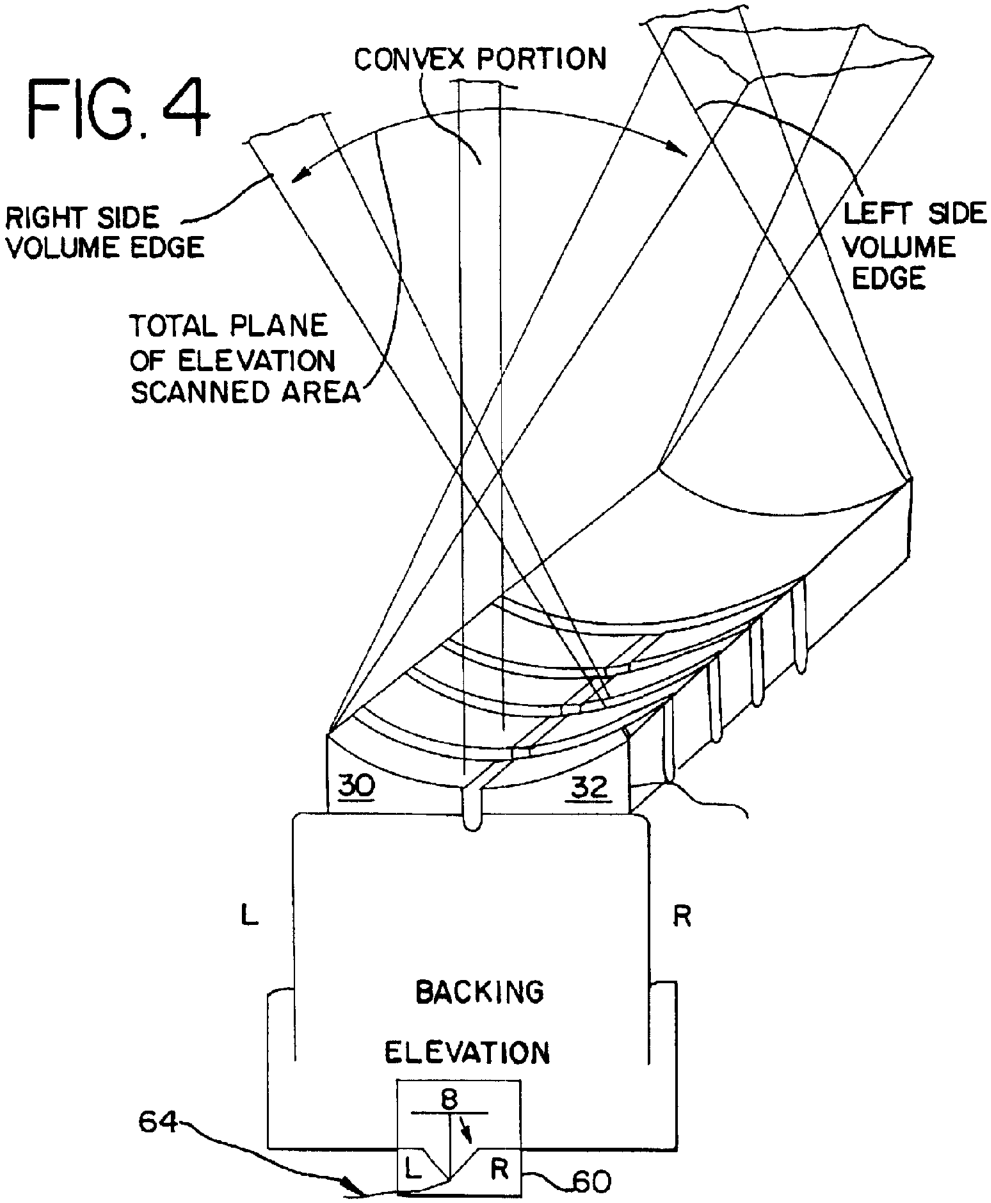
FIG. 4 illustrates the volume scanned by the transducer array shown in FIG. 2.

FIG. 4 illustrates the volume scanned by the transducer array shown in FIG. 2. More particularly FIG. 4 illustrates the expected volume scanned by exciting the left segment 30 of the transducer elements 24 first with a low frequency excitation signal such as 2 Megahertz to generate a beam that is emitted from the thicker portion of the left segment 30 which is thus tilted toward the right segments 32 of the transducer. Azimuthal frames are acquired as the frequency of the excitation signal is increased so that the exiting beam is emitted from the thinner portion of the left segment 30. Preferably at a high frequency of about 4 Megahertz the switching device 60 is switched to couple both the left and right segments 30 and 32 to the excitation signal so that both segments are generating an ultrasound beam from the thinner, center portion of each segments which provides high resolution. The frequency of the excitation signal is increased to about 4.5 Megahertz, the switching element 60 switches so that only the right segments 32 of each transducer array receives the excitation signal. The frequency of the excitation signal is lowered so that a beam is generated from the thicker portions of the right segments 32 which is tilted toward the left segment 30 of the transducer. Thus unlike the non-uniform thickness transducer described in U.S. Pat. Nos. 5,415,175 and 5,438,998 which did not divide each transducer element into two segments, for any selected frequency of excitation signal a left and a right azimuthal scan can be emitted to generate a volumetric scan. Thus the excitation of each transducer element is swept from one end of the transducer to the other. Electronic steering is performed in the y-azimuth direction as is well known.

Thus the present transducer array has the performance of an N×N array while only doubling the signal traces that are needed in a conventional one-dimensional array. In addition, the number of coaxial wires 64 in the cable 62 is only increased by two because of the switching element from a conventional one-dimensional transducer array. In addition, no positioner or mechanical registration is needed to perform two-dimensional scanning and three-dimensional imaging. Also, one can perform real-time three-dimensional imaging.

Figure 5:
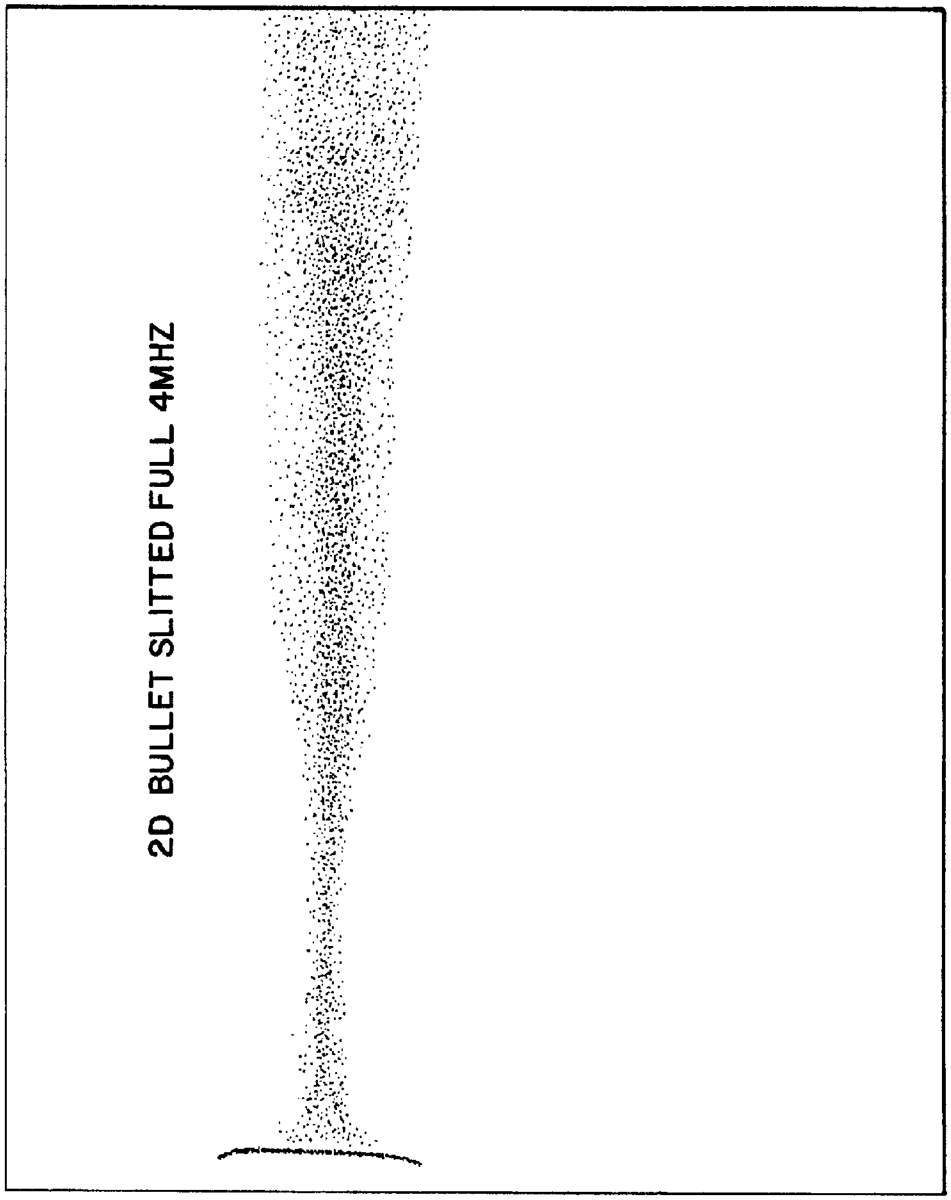
FIGS. 5–7 are actual schlieren images illustrating the operation of the transducer shown in FIG. 2.
Figure 6:
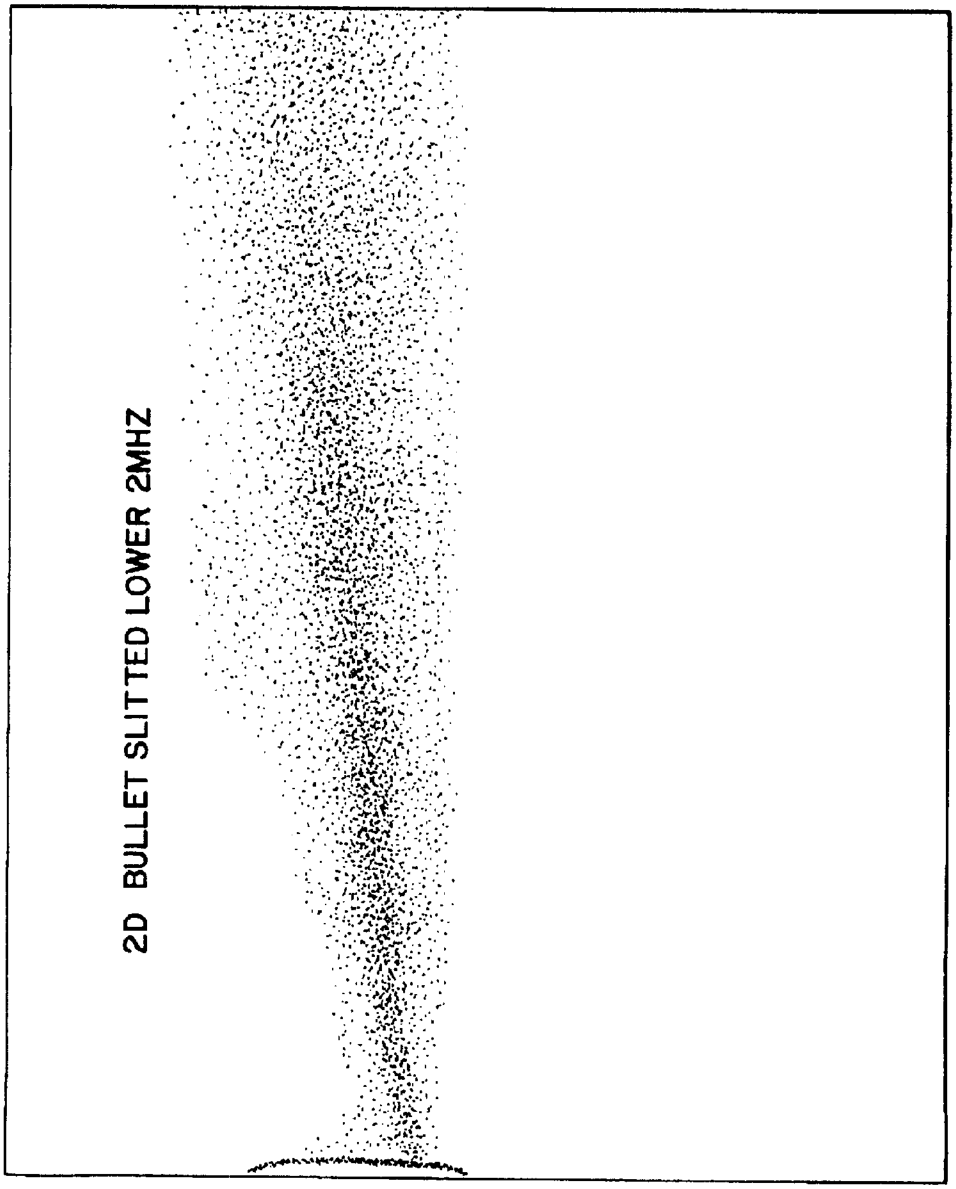
Figure 7:

FIGS. 5–7 are actual schlieren images illustrating the operation of the transducer according to FIG. 2.

In a preferred embodiment, an Acuson model 4V2C transducer array was modified to provide the electrically and acoustically isolated left and right halves. Each transducer element had a width in the x-elevation direction of about 15 mm and a width in the y-azimuth direction of 0.0836 mm. Each transducer element had a minimum thickness of 0.013 inches and a maximum thickness of 0.024 inches. Acoustic matching layer 38 had a minimum thickness of 0.004 inches and a maximum thickness of 0.007 inches. Acoustic matching layer 36 had a minimum thickness of 0.0048 inches and a maximum thickness of 0.008 inches. The band width of a single transducer element preferably ranges from 2.0 Megahertz to 4.5 Megahertz. The radius of curvature of the front surface of the transducer element is 2.9 inches thereby producing a transducer element with a 78% bandwidth. The backing block was formed of a filled epoxy comprising Dow Coming's part number DER 332 treated with Dow Coming's curing agent DEH 24 and an Aluminum Oxide filler. The backing block had a dimension of 20 mm in the y-azimuth direction, 16 mm in the x-elevation direction, and 20 mm in the z-range direction. The backing block, the flex circuit, the piezoelectric layer, and the matching layers, were glued together with an epoxy material and preferably a Hysol®. base material number 2039 having a Hysol®. Curing agent number HD3561, which is manufactured by Dexter Corp., Hysol Division of Industry, California was used for gluing the various materials together. Typically, the thickness of epoxy material is approximately 2 $\mu$m.

FIG. 5 shows the schlieren image when both the left and right segments were excited at 4 Megahertz. The exiting beam is emitted from the thinner center portion of each segment of the transducer element.

FIG. 6 shows the schlieren image when the right segment alone is excited with a low frequency signal (2 Megahertz), it can be seen that the exiting beam is emitted from the thicker portion of the transducer segment and the emitted beam tilts toward the segment not being excited. The same is true when the left segment is solely excited at a low frequency as shown in FIG. 7. Thus FIGS. 5–7 illustrate the frequency dependent x-elevation steering capability of the present invention.

Figure 8:
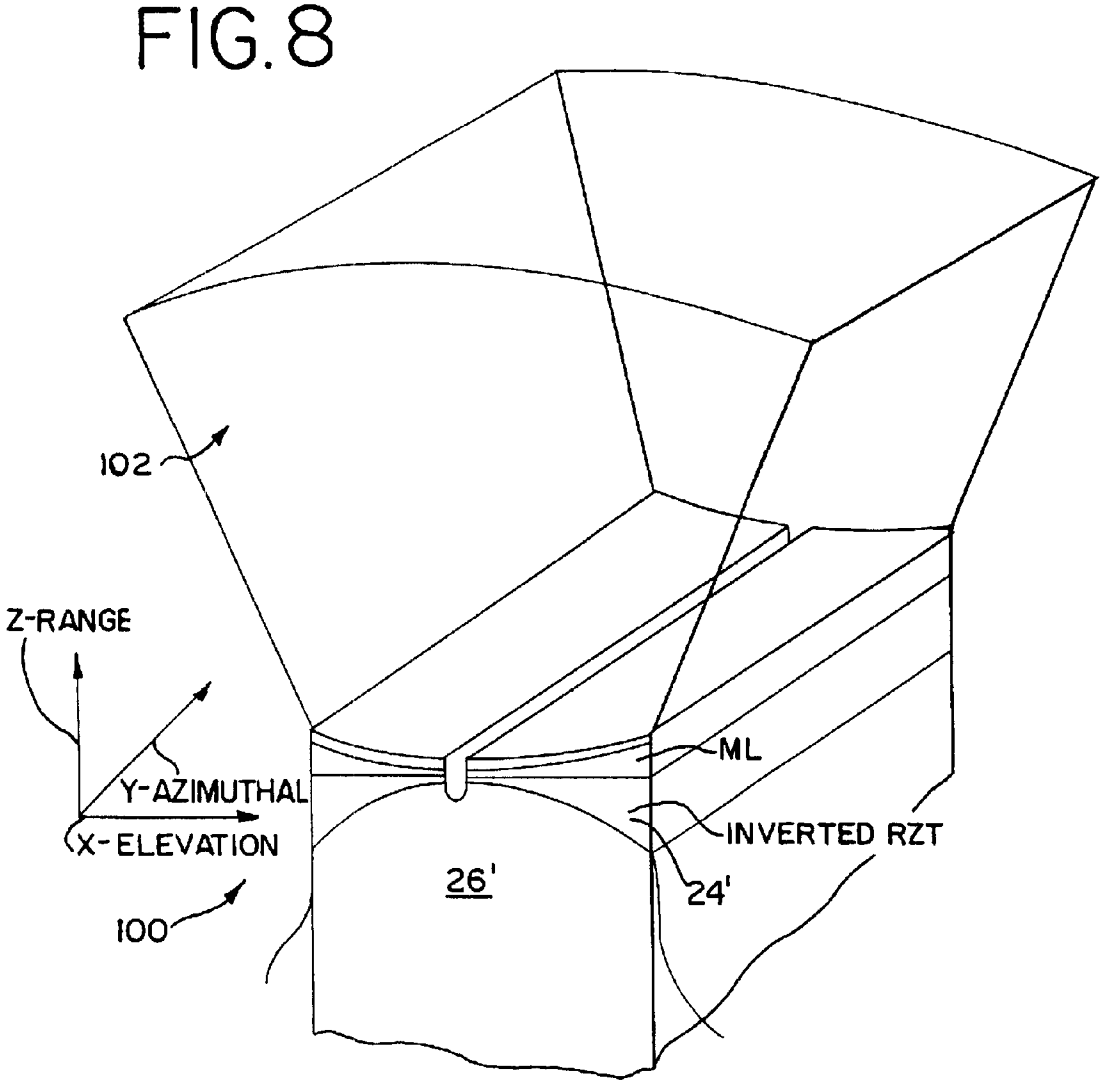
FIG. 8 is a perspective view of a portion of a transducer array according to another preferred embodiment of the present invention.

FIG. 8 is a perspective view of a portion of a transducer array 100 according to another preferred embodiment of the present invention. The transducer array shown in FIG. 8 has the same construction as that shown in FIG. 2 except that the curved face of each transducer element 24' is facing the backing block 26', not the object to be imaged. With the curved surface of each transducer element 24' facing the backing block the exiting beam is diverging so that a larger volume area can be scanned as shown by the volume 102.

Because the two-dimensional transducer array according to the present invention only has two segments in the x-elevation direction the impedance of the transducer is lower than N×N arrays such as that described earlier and thus make it easier to electrically match the transducer to the ultrasound system which typically has a low impedance.

While this invention has been shown and described in connection with the preferred embodiments, it is apparent that certain changes and modifications, in addition to those mentioned above, may be made from the basic features of the present invention. Accordingly, it is the intention of the Applicant to protect all variations and modifications within the true spirit and valid scope of the present invention.

I claim:

1. A method for two-dimensional scanning to produce three-dimensional images, the method comprising the steps of:

providing a plurally of transducer elements sequentially arranged in an azimuth direction wherein each transducer has a left and a right half, arranged in an elevation direction, said elevation direction being substantially perpendicular to said azimuth direction, that are electrically and acoustically isolated from one another so that the left and the right half can be independently excited, the plurality of transducer elements having a non-uniform thickness in a range direction, said range direction being substantially perpendicular to both said azimuth and said elevation directions;

applying an excitation signal to only the left half of the plurality of transducer elements;

progressively increasing the frequency of the excitation signal applied to the left half of the transducer elements;

coupling the left and right half of the transducer elements to a high frequency excitation signal;

applying an excitation signal to only the right half of the transducer elements; and progressively decreasing the frequency of the excitation signal applied to the right half of the transducer elements.

2. A method according to claim 1 wherein the frequency of the excitation signal ranges from about 2 Megahertz to about 4 Megahertz.

* * * * *